US010543157B2

(12) United States Patent
Davis et al.

(10) Patent No.: US 10,543,157 B2
(45) Date of Patent: Jan. 28, 2020

(54) METHOD OF TREATING A HAIR DISORDER WITH N-HYDROXYPYRIDINONES

(71) Applicant: The Procter & Gamble Company, Cincinnati, OH (US)

(72) Inventors: Michael Glenn Davis, Liberty Township, OH (US); Robert Scott Youngquist, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/581,187

(22) Filed: Apr. 28, 2017

(65) Prior Publication Data
US 2017/0312206 A1   Nov. 2, 2017

Related U.S. Application Data

(60) Provisional application No. 62/329,391, filed on Apr. 29, 2016.

(51) Int. Cl.
*A61K 8/49* (2006.01)
*A61Q 5/02* (2006.01)
*A61Q 1/10* (2006.01)
*A61K 8/27* (2006.01)
*A61Q 7/00* (2006.01)

(52) U.S. Cl.
CPC .............. *A61K 8/4926* (2013.01); *A61K 8/27* (2013.01); *A61K 8/4933* (2013.01); *A61Q 1/10* (2013.01); *A61Q 5/02* (2013.01); *A61Q 7/00* (2013.01); *A61K 2800/74* (2013.01)

(58) Field of Classification Search
CPC .................................................. A61K 31/555
See application file for complete search history.

(56) References Cited

U.S. PATENT DOCUMENTS

| 4,185,106 | A | 1/1980 | Dittmar et al. |
| 5,424,435 | A | 6/1995 | Hani et al. |
| 5,675,013 | A | 10/1997 | Hani et al. |
| 8,980,876 | B2 | 3/2015 | Schwartz et al. |
| 8,986,664 | B2 | 3/2015 | DiColandrea et al. |
| 2011/0060195 | A1 | 3/2011 | De Noray et al. |
| 2012/0003300 | A1 | 1/2012 | Isaacs et al. |
| 2012/0136007 | A1 | 5/2012 | Mootha et al. |
| 2013/0109664 | A1* | 5/2013 | Schwartz .............. A61K 31/555 514/188 |

FOREIGN PATENT DOCUMENTS

| CH | 353846 | A | 4/1961 |
| EP | 0800814 | A2 | 10/1997 |
| GB | 2207051 | A | 1/1989 |
| JP | S5655857 | A | 5/1981 |
| JP | S5810630 | A | 1/1983 |
| JP | S58165035 | A | 9/1983 |
| JP | H03152439 | A | 6/1991 |
| JP | 2001172159 | A | 6/2001 |
| JP | 2008007476 | A | 1/2008 |
| JP | 2009096777 | A | 5/2009 |
| JP | 2009137889 | A | 6/2009 |
| WO | WO2011051948 | A2 | 5/2011 |
| WO | WO2014027370 | A1 | 2/2014 |
| WO | WO2014095289 | A2 | 6/2014 |

OTHER PUBLICATIONS

U.S. Appl. No. 15/836,377, filed Dec. 8, 2017, Fisher et al.
All final and non-final office actions for U.S. Appl. No. 15/836,377.
Gleyzer et al, "Activation of a PGC-1-related Coactivator (PRC)-dependent Inflammatory Stress Program Linked to Apoptosis and Premature Senescence", Journal of Biological Chemistry (2013), 288 (12), 8004-8015.
Gohil et al., "Nutrient-sensitized screening for drugs that shift energy metabolism from mitochondrial respiration to glycolysis", Nature Biotechnology, vol. 28, 3, 2010 249-257.
Laura A. Wyness et al., "Trichotillometry: the reliability and practicality of hair pluckability as a method of nutritional assessment", Nutrition Journal, 2007, 6:9.
Makoto Akashi et al., "Noninvasive method for assessing the human circadian clock using hair follicle cells",PNAS, 2010, vol. 107, No. 35, 15643-15648.
PCT International Search Report and Written Opinion for PCT/US2017/030023 dated Sep. 22, 2017.
PCT International Search Report and Written Opinion for PCT/US2017/065541 dated Feb. 19, 2018.
Piérard-Franchimont et al., "Nudging hair shedding by antidandruff shampoos. A comparison of 1% ketoconazole, 1% piroctone olamine and 1% zinc pyrithione formulations", Int J Cosmet Sci. Oct. 2002;24(5):249-56.
"Some aspects of the mechanical behavior of hair" by WJ Hamburger, published in The Toilet Goods Association, No. 14, Dec. 1950.
"L'Oreal to launch new active to increase hair density", Andrew McDougall, Breaking News on Cosmetics Formulation & packaging in Europe, Jun. 21, 2012, http://www.cosmeticsdesign-europe.com/content/view/print/648430, 2 pages.
"Nudging hair shedding by antidandruff shampoos. A comparison of 1% ketoconazole, 1% piroctone olamine and 1% zinc pyrithione formulations", C. Pierard-Franchimont et al., International Journal of Cosmetic Science, 2002, 24, 249-256.

(Continued)

Primary Examiner — San Ming R Hui
(74) Attorney, Agent, or Firm — Linda M. Sivik

(57) ABSTRACT

The present invention is directed to a method for treating a hair disorder in a human or animal in need thereof, involving topically applying to the human or animal an effective amount of at least one 6-substituted 2-pyridinol N-oxide compound, a tautomer, or a cosmetically acceptable salt thereof wherein a hair count is increased by at least 0.5 hairs/cm$^2$ and/or an increase the number of anagen hairs and maintain the number of telogen hairs when compared to a baseline and/or vehicle.

18 Claims, No Drawings

(56) References Cited

OTHER PUBLICATIONS

P007: Hypoxia and Human Hair Follicle Stem/Progenitor Cells, Gaianne Gentry et al, L'Oreal Research and Innovation, Clichy, France, Int J Trichology, Apr.-Jun. 2012; 4(2). Abstract.

"Skin Rejuvenation through HIF-1a Modulation", Andrea Pagani et al, Special Topic, www.PRSJournal.com, vol. 141, No. 4, 8 pages, Apr. 2018.

\* cited by examiner

METHOD OF TREATING A HAIR DISORDER WITH N-HYDROXYPYRIDINONES

FIELD OF THE INVENTION

The present invention is directed to a method of treating a hair disorder by topically applying a 6-substituted 2-pyridinol N-oxide compound.

BACKGROUND OF THE INVENTION

Hair loss and skin appearance can have a profound effect on individuals' psychological well-being and quality of life. Anti-aging products represent a high percentage of skin and hair care product sales in the U.S. and abroad, and sales are expected to rise in many Western markets having an aging demographic. (Lennard, "Hair Care Growth Thinning for Near Term," Global Cosmetics Industry Magazine, May 2009.) Consumers seek these products to counteract age-related changes to epithelial biology that lead to skin imperfections (e.g., loss of elasticity, discoloration, dryness, and rough surface texture) and hair loss and thinning.

Thinning hair and significant hair loss, i.e., "baldness," is regarded in many cultures as less attractive. Hair growth is a cyclical process consisting of a growth stage (anagen), a regression stage (catagen), and a quiescent stage (telogen). During anagen, the hair bulb within the follicle penetrates the dermis and contacts the dermal papilla, triggering division of hair matrix keratinocytes. The new keratinocytes dehydrate and condense to form the hair shaft, which is pushed through the epidermis by newly dividing keratinocytes in the hair root. Hair growth ends in the catagen phase. The hair bulb separates from the dermal papilla, retracts from the dermis, and the follicle shrinks in size. In telogen, the hair remains attached to the follicle but, due to its shallow position in the epidermis, can easily be released from the skin. Normally, the follicle transitions back into anagen phase, during which the hair is pushed out of the follicle by hair newly formed by dividing keratinocytes. Disruption of the hair growth cycle leads to thinning and baldness. On the scalp, hair follicles shrink and shed terminal (long, pigmented) hair. The lost hair is either not replaced by new hair or is replaced by vellus (thin, short, non-pigmented) hair, resulting in the appearance of baldness.

The most common pharmacotherapeutics currently used to treat hair loss are minoxidil and 5-alpha reductase inhibitors, such as finasteride. The precise mechanism by which minoxidil reduces hair loss is unknown, and there is a significant percentage of patients that do not respond to therapy. (Lack of efficacy of finasteride in postmenopausal women with androgenetic alopecia, Journal of the American Academy of Dermatology, 43 (5), 768-776 (2000).) While finasteride has been shown to slow hair loss in men, the drug is associated with several side effects, including gynecomastia and sexual dysfunction. Both minoxidil and anti-androgens can require several weeks to impact hair count, and must be continued indefinitely on a daily basis to maintain effectiveness.

Traditional methods to measure efficacy include the counting of the number of hair fibers in a given area from a photograph (e.g. 1 cm2). Additional analysis of the same physical site on the scalp from images taken at two separate time points (i.e. 48 hours apart) can reveal the growth phase of the individual hairs (i.e. anagen or telogen). It is generally understood that this there is a correlation in such data and its relationship to the loss and retention of hairs on the head.

Thus, there exists a need for materials and methods for reducing or delaying the effects of age on epithelial biology, particularly with respect to hair loss and/or hair retention.

SUMMARY OF THE INVENTION

In an embodiment of the present invention, the present invention is directed to a method for treating a hair disorder in a human or animal in need thereof, comprising topically applying to the human or animal an effective amount of at least one 6-substituted 2-pyridinol N-oxide compound, a tautomer, or a cosmetically acceptable salt thereof wherein a hair count is increased by at least 0.5 hairs/cm$^2$ and/or an increase the number of anagen hairs and maintain the number of telogen hairs when compared to a baseline and/or vehicle.

DETAILED DESCRIPTION OF THE INVENTION

While the specification concludes with the claims particularly pointing and distinctly claiming the invention, it is believed that the present invention will be better understood from the following description.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair and scalp.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Treating a hair disorder" as used herein, means the following distinct benefits or a combination: 1.) stimulating or inducing the regrowth, 2.) reducing the loss or 3.) increasing the density and/or reducing the heterogeneity of the diameter of keratinous fibers in a mammal in need of the same with an effective amount of the composition.

"Comparison to baseline" as used herein, means a measure of the formulation efficacy, and compares a test result at time zero to a test result at a time after treatment.

"Comparison to vehicle" as used herein, means a measure of the efficacy of the test compound, and compares a test result of a formulation without test compound ("vehicle") to a test result of a formulation containing test compound.

It is to be understood that within the scope of this invention numerous potential and actual resonance structures and tautomers exist. Thus, for example, pyridine-N-oxide can be represented as resonance forms (I), (II), and (III) pictured below. And, for example, the tautomeric form of 2-pyridinol-N-oxide (IV) is 1-Hydroxy-2(1H)-pyridinone, as shown in structure (V) below. In the art, resonance structures are frequently represented by one single structure, such as (III), pictured below. It is to be understood that when this disclosure refers to a particular structure, all of the reasonable resonance structures and tautomers are included.

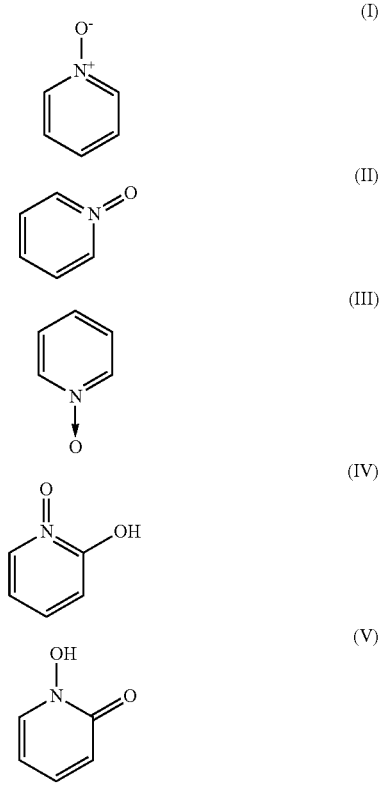

Without wishing to be bound by theory, it is found that actives that stabilize the expression of HIF-1α provide increased hair count and/or maintain hair count. Biological organisms have developed complex adaptive responses for regulating the delivery of enough oxygen and growth factors to cells to meet their metabolic demand. Many of these responses are linked by a family of transcriptional enhancer factors called Hypoxia Inducible Factors or HIF (Bunn N D Poyton, 1996; Semenza, 2000a). The HIF proteins are heterodimeric proteins that translocate to the nucleus and bind to cis acting enhancer element which amplify the transcription rate of those genes. There are 3 known HIFα subunits, HIF-1α, HIF-2α and HIF-3α. The Hif-1β subunit, also called the arylhydrocarbon nuclear translocator (ARNT) is constitutively expressed.

While HIF-1β is expressed constitutively, HIF-1α, HIF-2α and HIF-3α. are regulated in large part by HIF prolyl hydroxylases (PHDs) and Factor inhibiting HIF (FIH). In the presence of oxygen, iron and 2-oxoglutarate, PHD and FIH hydroxylate HIFα proline and asparagine residues, respectively. Hydroxylation of proline residues leads to proteolysis of HIF-α protein while the hydroxylated aspargine residue prevents HIFα interaction with transcriptional coactivators CBP/p300. Under conditions of low oxygen, low iron or low 2-oxoglutarate levels, PHD and FIH are inhibited and the HIF-α protein stabilizes, translocates to the nucleus and binds to HIF-1β and transcriptional coactivators. It is then that HIF then binds to response elements of target genes to induce their expression. Once activated, HIF can enhance the transcription of a variety of genes involved in angiogenesis, hematopoiesis and inflammation.

It has been proposed that positive regulation of HIF-1α can also positively impact hair biology with the intent to induce and/or stimulate the growth (size and number) or hair retention of human keratinous fibers, such as the hair and eyelashes, and/or slow down their loss. However, it has been found that such materials are less potent and selective than the present invention of N-hydroxypyridinones.

Additionally, factors such as Vascular Endothelial Growth Factor (VEGF), a HIF regulated gene, have already been show to accelerate hair growth, increase hair size and density in the overexpressed state. In fact, multiple HIF-1a target genes have been shown to be involved in hair follicle function.

Table of Known HIF Regulated Genes:

| | HIF Target Genes | | |
|---|---|---|---|
| Oxygen Supply | Cellular Metabolism | Cell Growth and Apoptosis | Others |
| Erythropoietin | Phosphofructokinase | IGFBP-1 | Cited2/p35srj |
| Globin-2 | Aldolase A | TGF-β3 | ID2 |
| Ferrochelatase | GAPDH | Endoglin | ETS-1 |
| BCRP | Phosphoglycerate kinase | CTGF | DEC1 |
| Transferrin | Enolase 1 | ITF | DEC2 |
| Transferrin receptor | Lactate dehydrogenase A | CD73 | Retrotransposon VL30 |
| Ceruloplasmin | Glucokinase | RORα4 | Human Herpesvirus 8 ORF34 |
| VEGF | PFKFB3 | RTP801/REDD1 | B19 erythrovirus |
| Flt-1/VEGF-R1 | PFKFB4 | SDF-1 | CD18 |
| Flk-1/VEGF-R2 | PEPCK | CXCR4 | GRP94 |
| Leptin | Glucose transporter 1 | Nur77 | Furin |
| iNOS | CAIX | Met | MT1 |

-continued

| HIF Target Genes | | | |
|---|---|---|---|
| Oxygen Supply | Cellular Metabolism | Cell Growth and Apoptosis | Others |
| eNOS | GPx-3 | Wt1 | Collagen |
| Heme oxygenase | CYP4B1 | TERT | PHD2 |
| Endothelin-1 | CYP3A6 | NIP3 | PHD3 |
| α1β-adrenergic | CYP2C11 | BNIP3 | |
| Adrenomedullin | MDR1 | Noxa | |
| PAI-1 | | PP5 | |
| ANP | | Mcl-1 | |
| | | Nucleophosmin | |

It therefore stands to reason that by inhibiting the aforementioned PHD enzyme, one can stabilize HIF-1α and positively impact hair follicle function and ultimately, hair growth and/or retention. Therefore, the present invention has found that N-hydropyridinones do inhibit the PHD enzyme activity and stabilize HIF-1α resulting in increased expression of target genes related to positive hair follicular function.

Materials for HIF Stabilization and VEGF Production

Materials suitable for us in this invention include a substituted or unsubstituted 2-pyridinol-N-oxide compound or a salt thereof. Included within the scope of this invention are tautomers of this compound, e.g., 1-Hydroxy-2(1H)-pyridinone. The substituted or unsubstituted 2-pyridinol-N-oxide compound and its corresponding tautomeric form, 1-Hydroxy-2(1H)-pyridinone, are shown below:

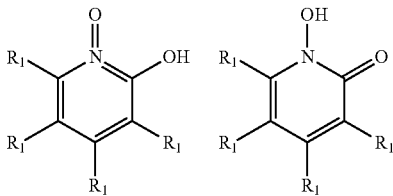

where each $R^1$ group is independently selected from the group consisting of H, Cl, Br, I, F, NO, $NO_2$, and $(CH_2)_nG$, where each G is independently selected from the group consisting of $(O)_mSO_3M$, $(O)_mCO_2M$, $(O)_mC(O)(R^2)$, $(O)_mC(O)N(R^2)_2$, $(O)_mCN$, $(O)_m(R^2)$, and $N(R^2)_2$, where each m is 0 or 1, each n is an integer from 0 to 4, each $R^2$ is independently selected from the group consisting of H and a substituted or unsubstituted $C_1$-$C_{12}$ organic group, and each M is independently selected from the group consisting of $R^2$ where $R^2$ is defined as above, $N^+(R^2)_4$, and $1/q\ M'^{q+}$ where M' is selected from the group consisting of an alkali metal of charge q and an alkaline earth metal of charge q, and where any two vicinal $R^1$ groups may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide compound is a 2-pyridinol-N-oxide compound or tautomer thereof according to the formula(s) above, where each $R^1$ is independently selected from the group consisting of H, Cl, and $(CH_2)_nG$, where G is independently selected from the group consisting of $(O)_mSO_3M$, $(O)_mCO_2M$, $(O)_mC(O)(R^2)$, $(O)_mCN$, and $(O)_m(R^2)$, where each m is 0 or 1. In other aspects, the 2-pyridinol-N-oxide compound is a 2-pyridinol-N-oxide compound according to the formula above, where each $R^1$ is independently selected from the group consisting of H, $SO_3M$, and $CO_2M$. In still other aspects, each $R^1$ is independently selected from the group consisting of H, $SO_3M$, and $CO_2M$, where no more than one $R^1$ is $SO_3M$ or $CO_2M$.

In certain aspects, the 2-pyridinol-N-oxide compound is the salt of a substituted or unsubstituted 2-pyridinol-N-oxide compound. In these aspects, the hydrogen of the hydroxyl group of the 2-pyridinol-N-oxide compound may be substituted with a suitable charge-balancing cation. In these aspects, non-limiting examples of the hydrogen-substituting cation include $Na^+$, $Li^+$, $K^+$, $\frac{1}{2} Mg^{2+}$, or $\frac{1}{2} Ca^{2+}$, substituted ammonium, such as $C_1$-$C_6$ alkanolammnonium, monoethanolamine (MEA), tri-ethanolamine (TEA), di-ethanolamine (DEA), or any mixture thereof. In some aspects, in solution, the cation may be dissociated from the 2-pyridinol-N-oxide or the 1-Hydroxy-2(1H)-pyridinone anion.

In certain aspects, the 2-pyridinol-N-oxide compound is of a substituted or unsubstituted 2-pyridinol-N-oxide compound. Salts for use herein include those formed from the polyvalent metals barium, bismuth, strontium, copper, zinc, cadmium, zirconium and mixtures thereof.

In some aspects, the 2-pyridinol-N-oxide compound is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These compounds are commercially available from, for example, Sigma-Aldrich (St. Louis, Mo.) and/or Aces Pharma (Branford, Conn.).

In certain aspects, the 2-pyridinol-N-oxide compound is a 2-pyridinol-N-oxide compound selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide compound is a 1-Hydroxy-2(1H)-pyridinone compound selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These compounds are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

In certain aspects, the 2-pyridinol-N-oxide compound is a 2-pyridinol-N-oxide compound or tautomer thereof according to the formula(s) below

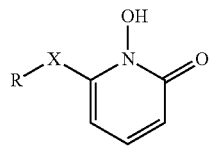

Where X is an oxygen or sulfur moiety and R is a substituted or unsubstituted hydrocarbon group having between 1 and 20 carbon atoms. Compounds of this class can be synthesized following the procedure disclosed in U.S. Pat. No. 5,675,013.

In certain aspects, the 2-pyridinol-N-oxide compound is a 2-pyridinol-N-oxide compound or tautomer thereof according to the formula(s) below

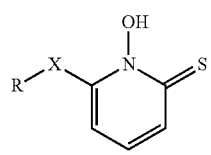

where X is an oxygen, sulfur, or NR' moiety wherein N is nitrogen and R and R' are independently each a substituted or unsubstituted hydrocarbon having between 1 and 20 atoms. Compounds of this class can be synthesized following the procedure disclosed in U.S. Pat. No. 5,675,013.

In certain aspects, the 2-pyridinol-N-oxide compound is a 2-pyridinol-N-oxide compound or tautomer thereof according to the formula(s) below

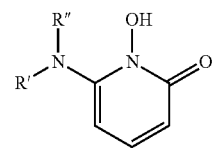

Wherein R' and R" are independently either hydrogen or a substituted or unsubstituted hydrocarbon group having between 1 and 20 carbon atoms. Compounds of this class can be synthesized following the procedure disclosed in U.S. Pat. No. 5,675,013.

In certain aspects, the 2-pyridinol-N-oxide compound is 1-hydroxy-6-(octyloxy)-2(1H)-Pyridinone. This compound can be synthesized following the procedure disclosed in U.S. Pat. No. 5,675,013.

Methods

In-Vitro Cell Based Method for Measuring HIF-1 Stabilization and VEGF Induction:

Human dermal fibroblasts are maintained and treated in Dulbecco's Modified Eagle Medium (DMEM) supplemented with 10% fetal bovine serum (FBS) and 1% penicillin/streptomycin.

For HIF and VEGF experiments, cells are plated at 10,000 cells per well in 96-well plates. After two days, cells are treated with materials of interest solubilized in DMSO. DMSO concentration in media never exceeded 0.5%. Treatment times are 4 hrs for HIF-1a and 24 hrs for VEGF. Analytes are assayed via ELISA. After 4 hrs treatment, cells are fixed and assayed for HIF-1a using the Human/Mouse Total HIF-1a Immunoassay (R&D Systems) according to manufacturer instructions. After 24 hrs treatment, spent culture media are harvested and assayed for VEGF using the V-PLEX Human VEGF Kit (MSD) according to manufacturer instructions. HIF-1a and VEGF signals are normalized to cytochrome c signal and ATP signal, respectively, and then compared to that of untreated control. Half-maximal effective concentrations of materials are calculating using GraphPad Prism version 6 software or any other suitable software.

TABLE 1

HIF-1α and VEGF data with various compounds:

| | $EC_{50}$ (μM) | |
|---|---|---|
| | HIF-1α Stabilization | VEGF Induction |
| N-Hydroxy-6-octyloxypyridine-2(1H)one | 17 | 30 |
| N-Hydroxy-6-octyloxypyridine-2(1H)one monoethanolamine* | 9 | 13 |
| 2,4-DPD* | 406 | no response |
| Minoxidil | >120 uM | >120 uM |
| 1-Hydroxy-4-methyl-6-(2,4,4-trimethylpentyl)pyridin-2(1H)-one ethanolammonium salt | 0.4 | 2.1 |

TABLE 1-continued

HIF-1α and VEGF data with various compounds:

| | EC$_{50}$ (μM) | |
|---|---|---|
| | HIF-1α Stabilization | VEGF Induction |
| 6-cyclohexyl-1-hydroxy-4-methyl-2(1H)-pyridinone | 3.9 | 2.5 |

*2,4-DPD = 2,4-pyridinedicarboxylic acid, diethyl ester, CAS # 41438-38-4 (aka Stemoxydine)
N-Hydroxy-6-octyloxypyridine-2(1H)one, CAS# 162912-64-3
N-Hydroxy-6-octyloxypyridine-2(1H)one, ethanolamine salt, CAS #162912-65-4
1-Hydroxy-4-methyl-6-(2,4,4-trimethylpentyl)pyridin-2(1H)-one ethanolammonium salt, CAS #68890-66-4
6-cyclohexyl-1-hydroxy-4-methyl-2(1H)-pyridinone, CAS #29342-05-0
Minoxidil CAS #38304-91-5

The table above shows the in-vitro cell based activity demonstrating that the potency and efficacy of N-Hydroxy-6-octyloxypyridine-2(1H)one is above and beyond 2,4-DPD (Stemoxydine) for HIF-1a stabilization and subsequent VEGF induction. Assay performed as described above.

Clinical Testing

Two randomized, double-blind, vehicle-controlled split-scalp studies are conducted as follows:

Method of Treating Scalp (Clinical Procedure)

Two weeks prior to the Baseline visit, subjects are randomized into one of the 2 treatment groups appearing in the table below.

TABLE 2

Treatment legs- study 1

| Treatment Group | Material/Product |
|---|---|
| 1 | ½ head (N = 95) with 1% N-Hydroxy-6-octyloxypyridine-2(1H)one vs. matched vehicle |
| 2 | ½ head (n = 35) with Rogaine ® for Women (2% minoxidil) vs. alcoholic vehicle control |

Subjects have the imaging sites located and tattoos placed within the imaging sites to mark the area that will be used for image capture. Three days post-tattoo placement, subjects will begin the pretreatment phase during which they applied their pretreatment products on the designated side of their scalp (left/right) for 11 days as a way of training subjects on the tonic application procedures. After the pretreatment phase has been completed, qualified subjects begin the 16-week treatment phase. Within each treatment group, left/right product assignments are randomized (tonic product and vehicle). In the first study subjects applied the assigned tonic product to the designated side of the scalp twice a day. The morning before each site visit, subjects wash and dry their hair and refrain from applying their test products and any styling aides until after their study visit has been completed. Subjects are instructed to wash hair at least every other day with a standard 2-in-1 shampoo during the entire washout and treatment phases. In the second study, after the pretreatment phase has been completed, subjects had their hair washed using the standard shampoo (½ head washing procedure) by a trained operator and blown dry by themselves. After washing hair (no treatment products and no styling products after washing), the two 1.8×1.8 cm imaging sites on the midfrontal/parietal scalp are clipped for hair count analysis as described below. Site staff then apply the two treatment products to the assigned sites (3×3 cm) on the scalp. Subjects return to the study site later in the day and site staff apply the 2nd application of treatment products for that day (i.e. twice a day tonic application) to each site. The following day, the subjects return to the test site and have their hair washed using the standard shampoo (½ head washing procedure) by site staff and blown dry themselves. Images of the two sites are captured for anagen hair count.

The following day and for every day during the 8-week treatment phase subjects returned to the study site in the morning and had their hair washed by site staff (½ head washing procedure) and blown dry by themselves in the morning before the 1st application of treatment products of the day. Site staff then apply the two treatment products to the assigned sites (3×3 cm) on the scalp. Subjects return to the study site later in the day and site staff apply the 2nd application of the treatment products for that day (i.e. twice a day tonic application) to each site.

Hair Count Method

An efficacy end point of these studies is the change from baseline in target area hair count (hairs/cm2) at week 8 and/or 16, as applicable. Initial hair count and growth phase assessments are performed at baseline and at weeks 8 and 16, as applicable, in a designated target area of the scalp identified by the mini tattoo applied at baseline. The assessments are performed using a 1.8-cm2 square template centered over the mini tattoo. Hair within the template is clipped to approximately 1 mm in length. Photographic imaging equipment is supplied by Canfield Scientific Inc (Fairfield, N.J.) and is used to take macrophotographs of the shaved target area. The equipment comprises a Nikon D-SLR camera body (Nikon Corporation, Tokyo, Japan), Nikkor 60 MM F2.8 lens (Nikon Corporation), and a Canfield Epiflash (Canfield Scientific Inc, Fairfield, N.J.) with a glass contact plate and is preset and locked for magnification, f-stop, and exposure control. The analysis of the hair count photographs is performed by Canfield's core imaging laboratory. (ref: Harness J A, Kohut B, Garner J, Canfield W, Canfield D, Bertolino A. *Evaluation of hair count and thickness measurements in male and female pattern hair loss using a computer-assisted technique*. Poster presented at: European Hair Research Society; Zurich, Switzerland, Jul. 7-9, 2005.) The same 1 cm$^2$ area is mapped among the baseline, week 8, and week 16 images using the dot tattoo as a reference. Each image is then assigned a definite tracking number and randomized before analysis. The compliant and validated Canfield Hair Metrix (Canfield Scientific Inc, Fairfield, N.J.) image analysis application measures the total number of hair fibers and number of telogen and anagen hair. A trained and validated imaging technician reviewed and accepted each of the measurements. Total hair amount, number of anagen hairs and the number of telogen hairs are reported as number of hairs/cm$^2$.

The method for measuring the ratio of anagen, catagen and telogen to the full cycle of growth in human scalp is accomplished by re-photographing the clipped site on both sides of the head 48 hours after initial clipping. By comparing this image with the baseline picture one can observe which hair fibers have grown (follicles in anagen) as the fibers actively growing have extended in length over the initial clipped length.

Statistical Model:

Statistical analysis is performed by a paired t-test and are conducted at a $p<0.05$ two-sided significance level. Statistical tests are performed for each time point separately, each treatment separately (a change from baseline analysis), and the treatment-related difference in the changes from baseline. This difference is formed as the active treatment side change from baseline (CFB) minus the vehicle side CFB. The statistical model is a simple one-sample mean, and the null hypothesis is that the population mean difference (for both the change from baseline (CFB) and the active minus control difference of CFBs) equals zero, versus the unequal alternative. All statistical analyses are performed in R (R Core Team (2015). R: A language and environment for statistical computing. R Foundation for Statistical Computing, Vienna, Austria. URL https://www.R-project.org/.)

TABLE 3

| Study #1 Total Hair Count Summary Statistics and p-values | | | | | | |
|---|---|---|---|---|---|---|
| | | Treatment | Change from Baseline | | Difference of CFBs | |
| | n | time | Mean +/− SE | Pvalue | Mean +/− SE | Pvalue |
| N-Hydroxy-6-octyloxypyridine-2(1H)one (1%) | 81 | 8 weeks | 6.15 +/− 1.91 | 0.002 | 3.94 +/− 1.71 | 0.019 |
| Vehicle for N-Hydroxy-6-octyloxypyridine-2(1H)one | 81 | 8 weeks | 2.21 +/− 1.69 | 0.252 | | |
| N-Hydroxy-6-octyloxypyridine-2(1H)one (1%) | 81 | 16 weeks | 3.11 +/− 1.79 | 0.071 | 3.27 +/− 1.73 | 0.045 |
| Vehicle for N-Hydroxy-6-octyloxypyridine-2(1H)one | 81 | 16 weeks | −0.16 +/− 1.68 | 0.886 | | |
| Minoxidil | 34 | 8 weeks | 14.3 +/− 2.98 | <0.0001 | 11.29 +/− 3.02 | 0.0004 |
| Vehicle for Minoxidil | 34 | 8 weeks | 3.05 +/− 2.98 | 0.31 | | |
| Minoxidil | 34 | 16 weeks | 14.83 +/− 3.53 | <0.0001 | 13.45 +/− 3.47 | 0.0005 |
| Vehicle for Minoxidil | 34 | 16 weeks | 1.38 +/− 3.53 | 0.69 | | |

*p-values are calculated on square root transformed data.

Table 3 presents results of the data analysis from study #1. The results obtained show that there is little or no effect associated with the vehicle treatment, whereas N-Hydroxy-6-octyloxypyridine-2(1H)one shows a significant increase in hair count from baseline and above vehicle treatment at week 8 & 16 (p=0.019 and p=0.045, respectively). Also represented is the data from treatment with minoxidil for comparison purposes as a benchmark. In this study, the response to N-Hydroxy-6-octyloxypyridine-2(1H)one is, on average, 29% of the minoxidil response.

In an embodiment of the present invention, the hair count is increased by at least 0.5 hairs/cm$^2$ when treated with N-Hydroxy-6-octyloxypyridine-2(1H)one when compared to baseline. In a further embodiment, the hair count is increased by at least 1 hairs/cm$^2$ when compared to baseline. In yet a further embodiment, the hair count is increased by at least 2 hairs/cm$^2$ when compared to baseline. In yet a further embodiment, the hair count is increased by at least 3 hairs/cm$^2$ when compared to baseline.

In an embodiment of the present invention, the hair count is increased by at least 0.5 hairs/cm$^2$ when treated with N-Hydroxy-6-octyloxypyridine-2(1H)one when compared to vehicle. In a further embodiment, the hair count is increased by at least 1 hairs/cm$^2$ when compared to vehicle. In yet a further embodiment, the hair count is increased by at least 2 hairs/cm$^2$ when compared to baseline. In yet a further embodiment, the hair count is increased by at least 3 hairs/cm$^2$ when compared to vehicle.

In an embodiment of the present invention, the hair count is increased by about 1.5% when treated with N-Hydroxy-6-octyloxypyridine-2(1H)one when compared to baseline.
Tables 4 and 5: Summary Statistics and p-Values after 8 and 16 Weeks of Treatment (Second Study)

TABLE 4

| Study #2 Total Hair Count Summary Statistics and p-values | | | | | | |
|---|---|---|---|---|---|---|
| | | Treatment | Change from Baseline | | Difference of CFBs | |
| | n | time | Mean +/− SE | Pvalue | Mean +/− SE | Pvalue |
| N-Hydroxy-6-octyloxypyridine-2(1H)one (0.9%) | 65 | 8 weeks | 10.13 +/− 1.15 | <0.0001 | 3.35 +/− 1.37 | 0.016 |
| Vehicle for N-Hydroxy-6-octyloxypyridine-2(1H)one | 65 | 8 weeks | 6.78 +/− 1.15 | <0.0001 | | |
| Minoxidil | 29 | 16 weeks | 12.93 +/− 1.77 | <0.0001 | 5.76 +/− 2.1 | 0.0068 |
| Minoxidil Vehicle | 29 | 16 weeks | 7.17 +/− 1.77 | <0.0001 | | |

*p-values are calculated on square root transformed data.

TABLE 5

| Study #2 Anagen and Telogen Hair Count Summary Statistics and p-values | | | | |
|---|---|---|---|---|
| | Change from Baseline | | Difference of CFBs | |
| | Mean +/− SE | Pvalue | Mean +/− SE | Pvalue |
| ANAGEN Hair counts | | | | |
| HP100 | 3.82 +/− 1.14 | 0.0009 | 3.18 +/− 1.22 | 0.0100 |
| HP100 Vehicle | 0.65 +/− 1.14 | 0.57 | | |
| Minoxidil | 8.66 +/− 1.75 | 0.0001 | 7.79 +/− 1.87 | 0.0001 |
| Minoxidil Vehicle | 0.86 +/− 1.75 | 0.62 | | |
| TELOGEN Hair counts | | | | |
| HP100 | 2.96 +/− 1.11 | 0.0084 | 0.51 +/− 1.21 | 0.67 |
| HP100 Vehicle | 2.44 +/− 1.11 | 0.029 | | |
| Minoxidil | −4.07 +/− 1.71 | 0.018 | −7.45 +/− 1.85 | 0.0001 |
| Minoxidil Vehicle | 3.38 +/− 1.71 | 0.049 | | |

Table 5 presents results of the data analysis for the number of growing hairs (i.e. number of anagen hairs) and for the number of resting hairs (i.e. number of telogen hairs). The results obtained show that there is little or no effect associated with the vehicle treatment in the number of anagen (growing) hairs, whereas N-Hydroxy-6-octyloxypyridine-2 (1H)one shows a significant increase in growing hairs above vehicle treatment at week 8. The results obtained show that there is little or no effect with N-Hydroxy-6-octyloxypyridine-2(1H)one in telogen (resting) hairs above vehicle treatment at week 8 ($p=0.67$). Also represented is the data from treatment with minoxidil for comparison purposes. In this study, the response to minoxidil is to increase the number of anagen hairs and decrease the number of telogen hairs versus baseline and vehicle responses. This demonstrates that HP-101, unlike minoxidil, will not cause telogen effluvium (shedding).

In an embodiment of the present invention, there is an increase in anagen hairs by at least 0.5 hairs/cm$^2$ when treated with N-Hydroxy-6-octyloxypyridine-2(1H)one when compared to baseline. In a further embodiment, there is an increase in anagen hairs by at least 1 hairs/cm$^2$ when compared to baseline. In yet a further embodiment, there is an increase in anagen hairs by at least 2 hairs/cm$^2$ when compared to baseline. In yet a further embodiment, there is an increase in anagen hairs by at least 3 hairs/cm$^2$ when compared to baseline.

In an embodiment of the present invention, there is an increase in anagen hairs by at least 0.5 hairs/cm$^2$ when treated with N-Hydroxy-6-octyloxypyridine-2(1H)one when compared to vehicle. In a further embodiment, there is an increase in anagen hairs by at least 1 hairs/cm$^2$ when compared to vehicle. In yet a further embodiment, there is an increase in anagen hairs by at least 2 hairs/cm$^2$ when compared to baseline. In yet a further embodiment, the hair count is increased by at least 3 hairs/cm$^2$ when compared to vehicle.

Cosmetically Acceptable Compositions

The N-hydroxypridinones may be formulated into a cosmetically acceptable composition for use as a shampoo, conditioner, or leave in treatment. The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

Detersive Surfactant

In an embodiment of the present invention, a shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

A shampoo composition described herein may comprise a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Shampoo Gel Matrix

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

In an embodiment of the present invention, the present invention may be in the form of a conditioner. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and in one embodiment a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

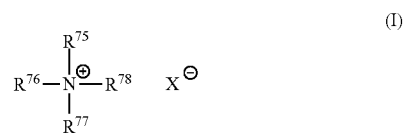

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one embodiment l-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

(II)

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%.

These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition may include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-on Treatment

In an embodiment of the present invention, the present invention may be in the form of a leave-on treatment described herein. The leave-on treatment may optionally comprise from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment may also comprises (1) one or more rheology modifiers and (2) a third aqueous carrier.

Rheology Modifier

In one embodiment the leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, Hydrolite, Kucel and/or combinations thereof.

In a further embodiment of the present invention, a solubilizer may be present. Nonlimiting examples of a solubilizer are Arlasolve and Tween 80.

Water Miscible Solvents

The carrier useful in embodiments of the hair care composition includes water and water solutions of lower alkyl alcohols, polyhydric alcohols, ketones having from 3 to 4 carbons atoms, C1-C6 esters of C1-C6 alcohols, sulfoxides, amides, carbonate esters, ethoxylated and proposylated C1-C10 alcohols, lactones, pyrollidones, and mixtures thereof. Non-limited lower alkyl alcohol examples are monohydric alcohols having 1 to 6 carbons, such as ethanol and isopropanol. Non-limiting examples of polyhydric alcohols useful herein include propylene glycol, dipropylene glycol, butylenes glycol, hexylene glycol, glycerin, propane diol and mixtures thereof.

Aqueous Carrier

The leave-on treatment may comprise a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from about 20 wt % to about 95 wt %, or from about 60 wt % to about 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Anti-Dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are one embodiment of a particulate anti-dandruff agents for use in compositions of the present invention. The concentration of pyridinethione anti-dandruff particulate typically ranges from about 0.1% to about 4%, by weight of the composition. In an embodiment, the concentration of pyridinethione anti-dandruff particulate ranges from about 0.1% to about 3%, and in a further embodiment, ranges from about 0.3% to about 2%. In an embodiment of the present invention, pyridinethione salts include those formed from heavy metals such as zinc, tin, cadmium, magnesium, aluminum and zirconium. In an embodiment of the present invention, a pyridinethione salts formed from a heavy metal zinc, and in a further embodiment, the zinc salt of 1-hydroxy-2-pyridinethione (known as "zinc pyridinethione" or "ZPT"), and yet a further embodiment of 1-hydroxy-2-pyridinethione salts in platelet particle form, wherein the particles have an average size of up to about 20μ. In an embodiment of the present invention, the particles have an average size up to about 5μ, and in a further embodiment up to about 2.5μ. Salts formed from other cations, such as sodium, may also be suitable. Pyridinethione anti-dandruff agents are described, for example, in U.S. Pat. Nos. 2,809,971; 3,236,733; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

2. Other Anti-Microbial Actives

In addition to the anti-dandruff active selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. In an embodiment of the present invention, anti-microbials include itraconazole, ketoconazole, selenium sulphide and coal tar.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%. In an embodiment of the present invention, the azole anti-microbial active is included in an amount from about 0.1% to about 3%, and in a further embodiment, from about 0.3% to about 2%, by weight of the composition. In an embodiment of the present invention, the azole anti-microbial is ketoconazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, and in an embodiment of the present invention, from about 0.3% to about 2.5%, and in a further embodiment from about 0.5% to about 1.5%. Selenium sulfide is generally regarded as a compound having one mole of selenium and two moles of sulfur, although it may also be a cyclic structure that conforms to the general formula $Se_xS_y$, wherein $x+y=8$. Average particle diameters for the selenium sulfide are typically less than 15 μm, as measured by forward laser light scattering device (e.g. Malvern 3600 instrument), and in an embodiment of the present invention, less than 10 μm. Selenium sulfide compounds are described, for example, in U.S. Pat. Nos. 3,152,046; 4,089,945; and 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, and in an embodiment of the present invention from about 2% to about 4%.

d. Keratolytic Agents

The present invention may further comprise one or more keratolytic agents such as Salicylic Acid.

e. Additional Anti-Microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, zinc pyrithione and climbasole and mixtures thereof. These actives, when used herein, are used at levels of from about 1% to about 4%, and in an embodiment of the present invention, from about 2% to about 4%.

E. Optional Ingredients

In accordance with embodiments of the present invention, the hair care composition may further comprise one or more optional ingredients, including benefit agents Suitable benefit agents include, but are not limited to conditioning agents, cationic polymers, silicone emulsions, anti-dandruff actives, gel networks, chelating agents, and, natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

EXAMPLES

The following non-limiting examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified.

Example 4

A tonic of the invention is prepared by conventional methods from the following exemplary components:

| Component | wt % | wt % | wt % |
|---|---|---|---|
| Alcohol 100% DEB 100 (Ethanol) | 25.00 | 20 | 20 |
| Dipropylene Glycol | — | 50 | 50 |
| 1-hydroxy-6-(octyloxy)-2(1H)-Pyridinone | 0.5 | 1 | |
| 1-Hydroxy-4-methyl-6-(2,4,4-trimethylpentyl)pyridin-2(1H)-one ethanolammonium salt | | | 0.75 |
| Carbomer (Carbopol Ultrez 10)[1] | 0.10 | — | — |
| Arlasolve[2] | — | 8 | 8 |
| Tween-80 | — | 10 | 10 |
| Hydrolite-5[3] | — | 10 | 10 |
| Klucel[4] | 1 | 1 | 1 |
| BHT | 0.50 | — | — |
| Triethanolamine | 0.20 | — | — |
| Deionized water | Qs | — | — |

[1]Carbopol Ultrez 10, carbomer, available from Lubrizol
[2]Arlasolve DMI, dimethyl isosorbide, available from Croda
[3]Hydrolite-5, pentylene glycol, available from Symrise
[4]Klucel, hydroxypropylcellulose, available from Ashland Example 5

A shampoo of the invention is prepared by conventional methods from the following exemplary components as described in International Patent Publication No. WO 2008/027541 and U.S. Patent Application Publication No. 20080059313:

| Component | Embodiment | | | | | |
|---|---|---|---|---|---|---|
| | 1 (wt %) | 2 (wt %) | 3 (wt %) | 4 (wt %) | 5 (wt %) | 6 (wt %) |
| Water | Q.S. | Q.S. | Q.S. | Q.S. | Q.S. | Q.S. |
| Rheology modifying system, anionic | 0.05 | 0.05 | — | — | — | — |
| Rheology modifying system, clay Hydrous | 0.05 | 0.05 | 0.05 | — | — | — |
| Hydroxypropyl | — | — | 0.10 | — | — | — |
| Polyquaternium 10 (Ucare | 0.50 | 0.50 | 0.50 | 0.50 | 0.5 | 0.50 |
| Coconut monoethanolamide | 1.09 | 1.03 | 1.03 | 1.50 | 1.5 | 1.50 |
| 1-hydroxy-6-(octyloxy)- | 0.5 | 1.00 | 0.75 | 1.00 | 1.0 | 1.00 |
| 1-Hydroxy-4-methyl-6-(2,4,4-trimethylpentyl)pyridin- | | | | | 0.5 | |
| 1-Hydroxy-4-methyl-6-cyclohexyl-2-pyridinone | | | | | | 0.75 |
| Disodium EDTA | 0.14 | 0.14 | 0.14 | 0.10 | 0.1 | 0.10 |
| Sodium Benzoate (Purox S | 0.25 | 0.25 | 0.25 | 0.25 | 0.2 | 0.25 |
| Sodium Citrate Dihydrate | 0.45 | 0.45 | 0.45 | 0.45 | 0.4 | 0.45 |
| Sodium Laureth-3-Sulfate | 2.18 | — | — | — | — | — |
| Cocamidopropyl Betaine | 2.18 | — | — | — | — | — |
| Sodium lauryl sulfate (SLS) | 6.55 | — | — | — | — | — |
| Citric Acid | 0.08 | — | — | 0.04 | 0.0 | 0.04 |
| BHT | 0.50 | 0.50 | 0.50 | 0.50 | 0.5 | 0.50 |
| Sodium Chloride | 0.25 | 0.75 | 0.50 | 0.01 | 0.0 | 0.01 |
| Sodium Hydroxide | 0.01 | — | — | — | — | — |
| Dimethicone (Viscasil | 1.35 | 1.35 | 1.35 | 1.35 | 1.3 | 1.35 |
| Ammonium Laureth-3- | 0.07 | 4.11 | 6.00 | 6.00 | 6.0 | 6.00 |
| Ethylene glycol distearate | 1.50 | 1.50 | 1.50 | 1.50 | 1.5 | 1.50 |
| Ammonium Lauryl Sulfate | 1.50 | 6.88 | 6.88 | 10.0 | 10. | 10.00 |

-continued

| Component | Embodiment 1 (wt %) | 2 (wt %) | 3 (wt %) | 4 (wt %) | 5 (wt %) | 6 (wt %) |
|---|---|---|---|---|---|---|
| Methylchloroisothiazolinone &Methylisothiazolinone | 0.0005 | 0.0005 | 0.0005 | 0.0005 | 0.0005 | 0.0005 |
| Fragrance | 0.70 | 0.70 | 0.70 | 0.70 | 0.7 | 0.70 |
| PEG 7M (Polyox WSR-N- | 0.10 | — | — | 0.10 | 0.1 | 0.10 |
| DL Panthenol 50% soln. | 0.03 | 0.03 | 0.03 | 0.03 | 0.0 | 0.03 |
| DL Panthenyl Ethyl Ether | 0.03 | 0.03 | 0.03 | 0.03 | 0.0 | 0.03 |
| Lysine Monochloride | 0.03 | 0.03 | 0.03 | 0.03 | 0.0 | 0.03 |
| L-Tyrosine Methylester Hydrochloride | 0.01 | 0.01 | 0.01 | 0.01 | 0.01 | 0.01 |
| Histidine | 0.01 | 0.01 | 0.01 | 0.01 | 0.0 | 0.01 |
| Cetyl Alcohol | | | | 0.90 | 0.9 | 0.90 |

1 Stabileze 06, poly(methylvinylether/maleic anhydride decadiene) crosspolymer, available from Ashland
2 Laponite XLS, sodium magnesium silicate, available from Eckart America
3 PrimaFlo HP22, hydroxypropylcellulose, available from Ashland
4 Ucare Polymer LR 400, polyquaternium-10, available from Dow
5 Monamid DMA, Coconut monoethanolamide, available from Croda
6 Tegobetaine F-B, Cocamidopropyl Betaine, available from Goldschmidt Chemicals
7 Viscasil 3000, 000,: dimethicone, available from Momentive
8 Polyox WSR N-750, PEG-7M, available from Dow
9 Kathon CG, available from Dow

Example 6

A conditioner of the invention is prepared by conventional methods from the following components as described in International Patent Publication No. WO 2008/027541 and U.S. Patent Application Publication No. 20080059313:

| Component | Embodiment 1 (wt %) | 2 (wt %) | 3 (wt %) | 4 (wt %) | 5 (wt %) |
|---|---|---|---|---|---|
| Dimethicone compound-1 [1] | | 4.20 | 4.20 | | |
| Dimethicone compound-2 [2] | — | — | — | 2.00 | 2.00 |
| Silicone compound-2 [3] | 3.50 | — | — | | |
| Behenyl trimethyl | 2.25 | — | — | 3.38 | 3.38 |
| Isopropyl alcohol | 0.60 | — | — | 0.90 | 0.90 |
| Stearamidopropyl | — | 2.00 | 2.00 | — | — |
| Glutamic acid [8] | — | 0.64 | 0.64 | — | — |
| Cetyl alcohol [9] | 1.90 | 2.50 | 2.50 | 2.30 | 2.30 |
| Stearyl alcohol [10] | 4.60 | 4.50 | 4.50 | 4.20 | 4.20 |
| 1-hydroxy-6-(octyloxy)-2(1H)-Pyridinone | 1.00 | | 1.00 | | 0.5 |
| 1-Hydroxy-4-methyl-6-(2,4,4-trimethylpentyl)pyridin- | | 0.75 | | | |
| 1-Hydroxy-4-methyl-6-cyclohexyl-2-pyridinone ethanolamine salt | | | | 0.5 | |
| Polysorbate-20 [11] | — | — | — | — | — |
| PPG-34 [12] | — | — | — | — | — |
| Polyalphaolefin [13] | — | — | — | — | — |
| BHT | 0.50 | 0.50 | 0.50 | 0.50 | 0.50 |
| Benzyl alcohol | 0.40 | 0.40 | 0.40 | 0.40 | 0.40 |
| Methylchloroisothiazolinone/ | 0.0005 | 0.0005 | 0.0005 | 0.0005 | 0.0005 |
| Perfume | 0.35 | 0.50 | 0.50 | 0.35 | 0.35 |
| NaOH | 0.014 | — | — | 0.014 | 0.014 |
| Panthenol [15] | 0.05 | — | — | 0.05 | 0.05 |
| Panthenyl ethyl ether [16] | 0.05 | — | — | 0.05 | 0.05 |
| Hydrolyzed collagen [17] | — | 0.01 | 0.01 | — | — |
| Vitamin E [18] | — | 0.01 | 0.01 | — | — |
| Decyl Glucoside [19] | — | — | — | — | — |
| Octyl methoxycinnamate | — | 0.09 | 0.09 | — | — |

-continued

| Component | Embodiment 1 (wt %) | 2 (wt %) | 3 (wt %) | 4 (wt %) | 5 (wt %) |
|---|---|---|---|---|---|
| Benzophenone-3 | — | 0.09 | 0.09 | — | — |
| Disodium EDTA | 0.13 | 0.13 | 0.13 | 0.13 | 0.13 |
| Deionized water | Qs | Qs | Qs | Qs | Qs |

[1] Dimethicone/Cyclomethicone: a blend dimethicone having a viscosity of 18,000,000 mPas and cyclopentasiloxane available from GE Toshiba
[2] Dimethicone blend: a blend of dimethicone having a viscosity of 18,000,000 mPas and dimethicone having a viscosity of 200 mPas available from GE Toshiba
[3] Available from GE having a viscosity 10,000 mPas, and having following formula (I): $(R_1)_a G3_a$-Si—(—$OSiG_2)_n$—(—$OSiG_b(R_1)_{2-b})_m$—O—$SiG_{3-a}(Ri)_a$ (I) wherein G is methyl; a is an integer of 1; b is 0, 1 or 2, preferably 1; n is a number from about 400 to about 600; m is an integer of 0; $R_1$ is a monovalent radical conforming to the general formula $C_qH_{2q}L$, wherein q is an integer of 3, and L is —$N(CH_3)_2$
[4] Behenyl trimethyl ammonium chloride/Isopropyl alcohol: Genamin KDMP available
[5] from Clariant
[6] Stearamidopropyl dimethylamine: Lexamine S-13 available from Inolex
[7] Glutamic acid: available from Ajinomoto
[8] Cetyl alcohol: Konol series available from Shin Nihon Rika.
[9] Stearyl alcohol: Konol series available from Shin Nihon Rika.
[10] Polysorbate-20: Glycosperse L-20K available from Lonza Inc.
[11] PPG-34: New Pol PP-2000 available from Sanyo Kasei.
[12] Polyalphaolefin: PureSyn 100 available from ExxonMobil Chemical Company
[13] Methylchloroisothiazolinone/Methylisothiazolinone: Kathon CG available from Rohm & Haas
[14] Panthenol: Available from Roche.
[15] Panthenyl ethyl ether: Available from Roche.
[16] Hydrolyzed collagen: Peptein 2000 available from Hormel.
[17] Vitamin E: Emix-d available from Eisai.
[18] Decyl glucoside: Plantacare 2000UP available from Cognis Japan Ltd.

Example 7

A mousse of the invention is prepared by conventional methods from the following exemplary components as described in International Patent Publication No. WO 2008/027541 and U.S. Patent Application Publication No. 20080059313:

| Component | wt % |
|---|---|
| Ethanol | 51.80 |
| Propylene glycol | 5.00 |
| Propellant (Propane) | 4.30 |
| Cetyl alcohol | 2.20 |
| Stearyl alcohol | 1.00 |
| 1-hydroxy-6-(octyloxy)-2(1H)-Pyridinone | 1.00 |
| Polyoxyethylene lauryl alcohol | 1.00 |
| BHT | 0.50 |
| Polysorbate 60 | 0.40 |
| Acetic acid (pH 6.0) | Qs |
| Deionized water | Qs |

Example 8

An oil-in-water mascara containing large wax particles and fibers is produced using the following exemplary components:

| Phase | Components | wt % |
|---|---|---|
| A | Glyceryl Monostearate | 5.250 |
| A | Black Iron Oxide | 7.25 |
| A | Disteardimonium Hectorite[1] | 2.250 |
| A | Stearic Acid | 2.750 |
| A | Carnauba Wax | 2.000 |
| A | Triethanolamine | 1.750 |
| A | Synthetic Wax | 1.500 |
| A | Polyvinyl Alcohol | 1.500 |
| A | Propylene Carbonate | 0.750 |
| A | 1-hydroxy-6-(octyloxy)-2(1H)-Pyridinone | 1.00 |
| A | Lecithin | 1.250 |
| A | Oleic Acid 80% | 1.000 |
| B | Acrylates Copolymer[2] | 5.170 |
| B | Deionized Water | 39.18 |
| B | Simethicone Emulsion 30%[3] | 0.200 |
| C | Xanthan Gum | 0.6 |
| C | Propylene Glycol | 3.000 |
| D | Ammonium Acrylates Copolymer[4] | 17.79 |
| E | Ethyl Alcohol SD 40-B | 1.000 |
| E | Benzyl Alcohol | 0.650 |
| E | Panthenol | 0.280 |
| E | Phenoxyethanol | 0.280 |
| E | Methylparaben | 0.200 |
| E | Ethylparaben | 0.200 |
| E | Propylparaben | 0.100 |
| E | Trisodium EDTA | 0.100 |
| F | Polyethylene Wax Particle (15-20 microns mean size)[5] | 3.000 |
| | TOTAL | 100.000 |

[1] Available as Bentone 38V from Elementis Specialties
[2] Available as Syntran 5190 from Interpolymer Corp.
[3] Available as Antifoam Q7-2587 from Dow Corning Corp.
[4] Available as Syntran KL-219C from Interpolymer Corp.
[5] Available as CeraPure H540-C from Shamrock Technologies Inc.

Phase A is heated to melt the waxes and allow the pigment to be dispersed with a Cowles Blade mixer or similar high energy dispersing device. Phase B materials are stirred together at ambient conditions, and Phase C materials are stirred together at ambient conditions and then it is added to Phase B (to gel Phase B), and the mixture is stirred and then heated to about 85 C. The Phase A and Phases B/C are mixed together to create an oil (wax) in water emulsion. The mixture is continuously stirred for 15 minutes and then is cooled gradually to room temperature. During the cool down, Phases D and E are added to the mixture and stirred in below 60 C. Phase F is spherical polyethylene wax particles that are prepared separately using typical process known in the art such as spray drying. Phase F is added to and mixed with the mascara once the mascara has cooled down to about 25 C.

Method of Production:

The polymeric materials such as the carboxylic acid/alkyl carboxylate copolymer, are dispersed in a portion of water at room temperature, mixed at a rotation speed controlled to no more than 5000 rpm, of by vigorous agitation, and heated to about 70 degrees centigrade until homogenous. A triblender can be used if necessary to disperse the polymeric materials. To this mixture, the silicone component and the emollient oil are added. The neutralizing agent, if present, is added to the mixture. After neutralizing, a water solution of the remaining components including tacky skin treatment agents, water soluble humectants, additional viscosity modifier, if present, and other components, if present, are added to the mixture, and then cooled to below 40 degrees centigrade.

Examples/Combinations

A. A method for treating a hair disorder in a human or animal in need thereof, comprising topically applying to the human or animal an effective amount of at least one 6-substituted 2-pyridinol N-oxide compound, a tautomer, or a cosmetically acceptable salt thereof wherein a hair count is increased by at least 0.5 hairs/cm$^2$ when compared to a baseline.

B. A method according to Paragraph A, wherein a hair count is increased by at least 0.5 hairs/cm$^2$ when compared to a vehicle.

C. A method for treating a hair disorder in a human or animal in need thereof, according to Paragraph A-B, comprising topically applying to the human or animal an effective amount of at least one 6-substituted 2-pyridinol N-oxide compound, a tautomer, or a cosmetically acceptable salt thereof wherein there is an increase in the number of anagen hairs by at least 0.5 hairs/cm$^2$ when compared to a baseline.

D. A method for treating a hair disorder in a human or animal in need thereof, according to Paragraph A-C, wherein there is an increase in the number of anagen hairs by at least 0.5 hairs/cm$^2$ when compared to vehicle.

E. A method for treating a hair disorder in a human or animal in need thereof, according to Paragraph A-D, comprising topically applying to the human or animal an effective amount of at least one 6-substituted 2-pyridinol N-oxide compound, a tautomer, or a cosmetically acceptable salt thereof wherein the number of telogen hairs is maintained when compared to a baseline.

F. A method for treating a hair disorder in a human or animal in need thereof, according to Paragraph A-E wherein the number of telogen hairs is maintained when compared to a vehicle.

G. A method according to Paragraph A-F, wherein the 6-substituted 2-pyridinol N-oxide compound is a metal salt selected from the group consisting of zinc salts, calcium salts, silver salts, nickel salts, magnesium salts, barium salts, bismuth salts and mixtures thereof.

H. A method according to Paragraph A-G, wherein said 6-substituted 2-pyridinol N-oxide is N-Hydroxy-6-octyloxypyridine-2(1H)one.

I. A method according to Paragraph A-H, wherein the hair count is increased by at least 1 hairs/cm$^2$ when compared to baseline.

J. A method according to Paragraph A-I, wherein the hair count is increased by at least 2 hairs/cm$^2$ when compared to baseline.

K. A method according to Paragraph A-J, wherein the hair count is increased by at least 3 hairs/cm$^2$ when compared to baseline.

L. A method according to Paragraph A-K, wherein the hair count is increased by about 1.5% when compared to baseline.

M. A method according to Paragraph A-L, wherein the hair count is increased by about 1.5% when compared to vehicle.

N. A method according to Paragraph A-M, wherein the composition further comprises a pyridinethione salts or a metal salt of a pyridinethione salt.

O. A method according to Paragraph A-N, wherein the composition further comprises zinc pyrithione.

P. A method according to Paragraph A-O, wherein the composition further comprises a rheology modifier.

Q. A method according to Paragraph A-P, wherein the composition further comprises a water miscible solvent.

R. A method according to Paragraph A-Q, wherein the composition further comprises a material selected from the group consisting of conditioning agents, cationic polymers, silicone emulsions, anti-dandruff actives, gel networks, chelating agents, natural oils, perfumes, perfume microcapsules, colorants, particles, anti-microbials, foam busters, anti-static agents, suspension materials, structurants, pH adjusting agents and buffers, preservatives, pearlescent agents, solvents, diluents, anti-oxidants, vitamins and mixtures thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

All documents cited in the Detailed Description of the Invention are, in relevant part, incorporated herein by reference; the citation of any document is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for treating a hair loss disorder in a human or animal in need thereof, comprising topically applying to the human or animal an effective amount of at least one 6-substituted 2-pyridinol N-oxide compound, a tautomer, or a cosmetically acceptable salt thereof wherein a hair count is increased by at least 0.5 hairs/cm$^2$ when compared to a baseline.

2. A method according to claim 1 wherein a hair count is increased by at least 0.5 hairs/cm$^2$ when compared to a vehicle.

3. A method for treating a hair loss disorder in a human or animal in need thereof, comprising topically applying to the human or animal an effective amount of at least one 6-substituted 2-pyridinol N-oxide compound, a tautomer, or a cosmetically acceptable salt thereof wherein there is an increase in the number of anagen hairs by at least 0.5 hairs/cm$^2$ when compared to a baseline.

4. A method for treating a hair loss disorder in a human or animal in need thereof, according to claim 3 wherein there is an increase in the number of anagen hairs by at least 0.5 hairs/cm$^2$ when compared to vehicle.

5. A method for treating a hair loss disorder in a human or animal in need thereof, comprising topically applying to the human or animal an effective amount of at least one 6-substituted 2-pyridinol N-oxide compound, a tautomer, or a cosmetically acceptable salt thereof wherein the number of telogen hairs is maintained when compared to a baseline.

6. A method for treating a hair loss disorder in a human or animal in need thereof, according to claim 5 wherein the number of telogen hairs is maintained when compared to a vehicle.

7. A method according to claim 1 wherein the 6-substituted 2-pyridinol N-oxide compound is a metal salt selected from the group consisting of zinc salts, calcium salts, silver salts, nickel salts, magnesium salts, barium salts, bismuth salts and mixtures thereof.

8. A method according to claim 1 wherein said 6-substituted 2-pyridinol N-oxide is N-Hydroxy-6-octyloxypyridine-2(1H)one.

9. A method according to claim 1 wherein the hair count is increased by at least 1 hairs/cm$^2$ when compared to baseline.

10. A method according to claim 1 wherein the hair count is increased by at least 2 hairs/cm$^2$ when compared to baseline.

11. A method according to claim 1 wherein the hair count is increased by at least 3 hairs/cm$^2$ when compared to baseline.

12. A method according to claim 1 wherein the hair count is increased by about 1.5% when compared to baseline.

13. A method according to claim 1 wherein the hair count is increased by about 1.5% when compared to vehicle.

14. A method according to claim 1 wherein the composition further comprises a pyridinethione salts or a metal salt of a pyridinethione salt.

15. A method according to claim 14 wherein the composition further comprises zinc pyrithione.

16. A method according to claim 1 wherein the composition further comprises a rheology modifier.

17. A method according to claim 1 wherein the composition further comprises a water miscible solvent.

18. A method according to claim 1 wherein the composition further comprises a material selected from the group consisting of conditioning agents, cationic polymers, silicone emulsions, anti-dandruff actives, gel networks, chelating agents, natural oils, perfumes, perfume microcapsules, colorants, particles, anti-microbials, foam busters, anti-static agents, suspension materials, structurants, pH adjusting agents and buffers, preservatives, pearlescent agents, solvents, diluents, anti-oxidants, vitamins and mixtures thereof.

* * * * *